United States Patent [19]
Yu

[11] 4,393,061
[45] Jul. 12, 1983

[54] ANESTHETIC-ANTIPRURITIC MORPHOLINE COMPOUNDS, COMPOSITIONS AND USE

[75] Inventor: Cheng-Sein Yu, Kaohsiung, Taiwan

[73] Assignee: Stiefel Laboratories, Inc., Coral Gables, Fla.

[21] Appl. No.: 390,572

[22] Filed: Jun. 21, 1982

[51] Int. Cl.³ .................. C07D 295/08; A61K 31/535
[52] U.S. Cl. ................................ 424/248.58; 544/174
[58] Field of Search .................... 544/174; 424/248.58

[56] References Cited

U.S. PATENT DOCUMENTS 2,870,151  1/1959  Wright et al. ....................... 544/174

FOREIGN PATENT DOCUMENTS 45-9937  4/1970  Japan .

Primary Examiner—Robert W. Ramsuer
Attorney, Agent, or Firm—Bruce M. Collins

[57] ABSTRACT

N-[3-(4-{3-Fluorobenzyloxy}phenoxy)propyl]morpholine and its pharmaceutically acceptable salts possess topical anesthetic-antipruritic properties. The free base can be obtained by coupling an alkali metal salt of 4-(3-fluorobenzyloxy)phenol and N-(3-chloropropyl)morpholine.

6 Claims, No Drawings

ANESTHETIC-ANTIPRURITIC MORPHOLINE COMPOUNDS, COMPOSITIONS AND USE

DETAILED DESCRIPTION

The present invention pertains to novel compounds having anesthetic-antipruritic properties and to compositions and methods utilizing these compounds.

It is an object of the present invention to provide compounds and compositions having topical anesthetic and antipruritic activities coupled with a low index skin sensitivity, low systemic toxicity and enhanced penetration through intact skin.

The compounds of this invention include the free base of the formula:

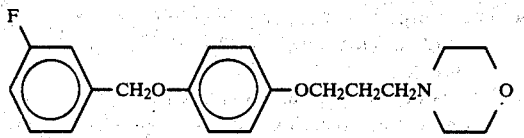

and the pharmaceutically acceptable acid addition salts thereof.

The free base of the above formula readily can be prepared by coupling N-(3-chloropropyl)morpholine and an alkali metal salt of 4-(3-fluorobenzyloxy)phenol in a suitable organic solvent. The 4-(3-fluorobenzyloxy)phenol starting material can be prepared by coupling hydroquinone, as an alkali metal salt, and 3-fluorobenzyl bromide.

In addition to the free base, the present invention also pertains to the pharmaceutically acceptable salts thereof, as for example the hydrohalide salts, most notably the hydrochloride, and those of sulfuric acid, phosphoric acid, methanesulfonic acid, tartaric acid, and the like. While such salts exhibit the anesthetic properties of their organic cation, they also demonstrate physical properties which often make them more suitable for pharmaceutical formulation.

The compounds are administered topically in conventional topical pharmaceutical formulation as for example creams, gels, ointments, lotions, solutions, and the like. As with all therapeutic agents of this type, such formulations should be applied as required, utilizing only as much as is needed to obtain the desired response. A 0.5 to 2% formulation typically is suitable to produce local anesthetic or an antipruritic response. The compounds can be administered in combination with other therapeutic agents, such as for example antiseptics, anti-inflammatory agents, antibiotics, antifungal agents, and the like.

The following examples will serve to further typify the present invention but should not be construed as a limitation on the scope thereof.

EXAMPLE 1

To a solution of 0.56 g (0.01 mol) of potassium hydroxide in 18 ml of absolute ethanol are added 2.18 g (0.01 mol) of 4-(3-fluorobenzyloxy)phenol. There is then added a solution of 1.64 g (0.01 mol) of N-(3-chloropropyl)morpholine in 2 ml of absolute ethanol. The mixture is stirred at reflux for 24 hours, allowed to cool and then refrigerated. The solid which forms is collected by filtration, washed with absolute ethanol and dissolved in diethyl ether. The ethereal solution is washed consecutively with water (20 ml), 10% aqueous sodium hydroxide (3×15 ml) and water until neutral to litmus. The solution is dried over sodium sulfate, filtered and evaporated and recrystallized from diethyl ether-petroleum ether and from diethyl ether alone to yield N-[3-(4-{3-fluorobenzyloxy}phenoxy)propyl]morpholine.

Alternatively 4-(3-fluorobenzyloxy)phenol (1.09 g, 0.005 mol) is added to a refluxing solution of potassium hydroxide (0.28 g, 0.005 mol) in absolute ethanol (10 ml). To this is then added a solution of N-(3-chloropropyl)morpholine (0.82 g, 0.005 mol) in absolute ethanol (2 ml). After heating at reflux for 24 hours, the solution is cooled and filtered. The solid is dissolved in ethyl ether. The ethereal solution is filtered to remove potassium chloride and concentrated. Addition of absolute ethanol produces formation of a solid which is collected and recrystallized from diethyl ether.

N-[3-(4-{3-Fluorobenzyloxy}phenoxy)propyl]morpholine (free base) when prepared according to the above procedures forms off-white crystals having a melting point of 88° to 89° C. Infrared analysis (potassium bromide pellet, cm$^{-1}$) will show bands at 3030, 1870, 1640, 1610, 1505, 1450, 2980–2750, 1470, 1230 and 1025. PMR (CDCl$_3$δ), will show peaks at 2.03 ppm (m, 2H, CH$_2$CH$_2$CH$_2$), 2.53 ppm (m, 6H, NCH$_2$), 3.64 ppm (complex m, 6H, OCH$_2$), 5.01 ppm (s, 2H, FC$_6$H$_4$CH$_2$O), 6.86 ppm (s, 4H, OC$_6$H$_4$O) and 7.26 ppm (m 4H, FC$_6$H$_4$). A representative elemental analysis is as follows:

For C$_{20}$H$_{24}$O$_3$NF (354.398) Calc. C,69.54; H,7.00; N,4.06; F,5.50 Found: C,69.37; H,7.20; N,3.96; F,5.44

N-(3-Chloropropyl)morpholine is a known compound.

4-(3-Fluorobenzyloxy)phenol can be prepared by adding 3-fluorobenzyl bromide (4.85 g, 0.025 mol) to a solution of hydroquinone (2.7 g, 0.025 mol) in aqueous sodium hydroxide (1.0 g of sodium hydroxide in 10 ml of water) under an inert atmosphere (nitrogen or argon). The mixture is stirred for one hour at room temperature and then heated at reflux for 24 hours. Upon cooling, the mixture is extracted with diethyl ether. These extracts are washed with water and in turn extracted with 10% aqueous sodium hydroxide. The aqueous extracts are washed with ether and rendered acidic. The solid which forms is collected by filtration, washed with water, dried and recrystallized from diethyl ether-petroleum ether. Its melting point is 102° to 103° C.

EXAMPLE 2

Hydrogen chloride is bubbled through a solution of 0.75 g of N-[3-(4-{3-fluorobenzyloxy}phenoxy)propyl]morpholine in 60 ml of diethyl ether. The solid which forms is collected by filtration and recrystallized from absolute ethanol to yield the hydrochloride salt.

The hydrochloride salt of N-[3-(4-{3-fluorobenzyloxy}phenoxy)propyl]morpholine when prepared according to the above procedure forms fine white crystals having a melting point of 186°–187° C. Infrared analysis shows similar bands to those for the free base plus several band at 2360–2700 (amine salt).

EXAMPLE 3

| Anesthetic-antipruritic Cream | |
|---|---|
| N—[3-(4-{3-Fluorobenzyloxy}-phenoxy)propyl]morpholine HCl | 5 parts (w) |
| Propylene glycol | 285 parts (w) |
| Carbowax 6000 | 210 parts (w) |

| -continued |  |
| --- | --- |
| Anesthetic-antipruritic Cream | |
| Total | 500 parts (w) |

The above ingredients are thoroughly blended to yield a 1% anesthetic-antipruritic cream suitable for topical application.

EXAMPLE 4

One part by weight of N-[3-(4-{3-fluorobenzyloxy}-phenoxy)-propyl]morpholine HCl is added to 98.1 parts by weight of sterile, deionized water. To this is added 0.9 parts by weight of benzyl alcohol. These ingredients are thoroughly blended to produce an anesthetic-antipruritic solution.

EXAMPLE 5

One part of weight of N-[3-(4-{3-fluorobenzyloxy}-phenoxy)-propyl]morpholine HCl is mixed with 75 parts by weight of sterile, deionized water. There are then added 20 parts by weight of propylene glycol and 4 parts by weight methacel. The ingredients are thoroughly blended to produce an anesthetic-antipruritic jelly.

What is claimed is:

1. A compound selected from the group consisting of the free base of the formula:

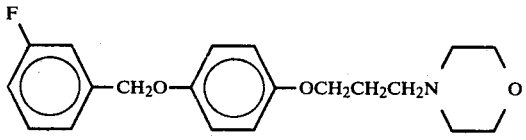

and the pharmaceutically acceptable acid addition salts thereof.

2. The compound according to claim 1 which is N-[3-(4-{3-fluorobenzyloxy}phenoxy)propyl]morpholine.

3. A compound according to claim 1 which is a pharmaceutically acceptable acid addition salt of N-[3-(4-{3-fluorobenzyloxy}phenoxy)propyl]morpholine.

4. The compound according to claim 3 which is N-[3-(4-{3-fluorobenzyloxy}phenoxy)propyl]morpholine hydrochloride.

5. The method of producing an anesthetic-antipruritic effect in an animal which comprises topically applying an effective amount of a compound according to claim 1.

6. A topical pharmaceutical composition comprising a compound according to claim 1 in an amount sufficient to produce a topical anesthetic-antipruritic effect, in combination with a carrier which is pharmaceutically acceptable for topical application.

* * * * *